(12) United States Patent
Pursley

(10) Patent No.: US 7,776,380 B2
(45) Date of Patent: *Aug. 17, 2010

(54) METHOD OF MAKING CATHETERS WITH ADDITIVES CONSOLIDATED INTO POLYMER WALL

(75) Inventor: Matt D. Pursley, Alpharetta, GA (US)

(73) Assignee: Volcano Corporation, Rancho Cordova, CA (US)

( * ) Notice: Subject to any disclaimer, the term of this patent is extended or adjusted under 35 U.S.C. 154(b) by 1271 days.

This patent is subject to a terminal disclaimer.

(21) Appl. No.: 11/234,514

(22) Filed: Sep. 22, 2005

(65) Prior Publication Data

US 2006/0062895 A1    Mar. 23, 2006

Related U.S. Application Data

(60) Provisional application No. 60/612,673, filed on Sep. 22, 2004.

(51) Int. Cl.
    A61M 25/00    (2006.01)
    B05D 3/02     (2006.01)
    B05D 1/02     (2006.01)
    B05D 1/36     (2006.01)

(52) U.S. Cl. .............. 427/2.1; 427/2.24; 427/2.25; 427/2.28; 427/296; 427/421.1; 427/426; 427/427.7; 604/264; 604/523; 600/139; 600/400

(58) Field of Classification Search ............... 427/2.1, 427/2.24, 2.25, 2.28, 296, 421.1, 426, 427.7; 607/122; 604/264, 523; 600/139, 140
See application file for complete search history.

(56) References Cited

U.S. PATENT DOCUMENTS

| 1,802,120 A | 4/1931  | Maynard         |
| 3,009,209 A | 11/1961 | Weinbrenner et al. |
| 3,019,014 A | 1/1962  | Miksis          |
| 3,369,922 A | 2/1968  | Svrchek         |
| 3,736,202 A | 5/1973  | Sorenson        |
| 3,749,621 A | 7/1973  | Shoffner        |
| 3,800,798 A | 4/1974  | Winkler         |
| 4,025,664 A | 5/1977  | Gerek et al.    |
| 4,026,747 A | 5/1977  | DeLorean et al. |
| 4,385,635 A | 5/1983  | Ruiz            |
| 4,577,543 A | 3/1986  | Wilson          |

(Continued)

Primary Examiner—Timothy H Meeks
Assistant Examiner—Cachet I Sellman
(74) Attorney, Agent, or Firm—Jeffrey L. Thompson; Thompson & Thompson, P.A.

(57) ABSTRACT

A method of making catheters is disclosed in which various additives are consolidated into polymer walls of the catheters. The method includes providing a core, spraying a base polymer material over the outer surface of the core, spraying an additive material over or together with the base polymer material, and consolidating the additive material and the base polymer material together to form the catheter wall. The base polymer material and additive material are each applied as a fine particulate powder or solution of fine particulate, which can be sprayed over an outer surface of the core and the catheter wall as the catheter is formed. The additive material can be selected from several therapeutic agents, diagnostic agents, and/or polymers for modifying the base polymer materials. The additive material can be consolidated with the base polymer material throughout the polymer wall or primarily on the outer surface of the polymer wall.

21 Claims, 1 Drawing Sheet

U.S. PATENT DOCUMENTS

| | | |
|---|---|---|
| 4,616,064 A | 10/1986 | Zukosky et al. |
| 4,636,346 A | 1/1987 | Gold et al. |
| 4,686,124 A | 8/1987 | Onohara et al. |
| 4,705,511 A | 11/1987 | Kocak |
| 4,722,344 A | 2/1988 | Cambron et al. |
| 4,764,324 A | 8/1988 | Burnham |
| 4,817,613 A | 4/1989 | Jaraczewski et al. |
| 5,013,717 A * | 5/1991 | Solomon et al. ............... 514/56 |
| 5,037,404 A | 8/1991 | Gold et al. |
| 5,057,092 A | 10/1991 | Webster, Jr. |
| 5,085,649 A | 2/1992 | Flynn |
| 5,116,652 A | 5/1992 | Alzner |
| 5,127,975 A | 7/1992 | Zackrisson et al. |
| 5,178,902 A | 1/1993 | Wong et al. |
| 5,250,059 A * | 10/1993 | Andreas et al. |
| 5,290,230 A | 3/1994 | Ainsworth et al. |
| 5,334,169 A | 8/1994 | Brown et al. |
| 5,516,560 A | 5/1996 | Harayama et al. |
| 5,558,652 A | 9/1996 | Henke |
| 5,749,837 A | 5/1998 | Palermo et al. |
| 6,030,371 A * | 2/2000 | Pursley ........................ 604/527 |
| 6,086,970 A * | 7/2000 | Ren .......................... 428/36.9 |
| 6,702,830 B1 * | 3/2004 | Demarais et al. ............ 606/159 |
| 2002/0002353 A1 * | 1/2002 | Michal et al. ................ 604/265 |
| 2002/0150671 A1 * | 10/2002 | Koulik et al. .............. 427/2.24 |
| 2003/0060783 A1 * | 3/2003 | Koole et al. ................. 604/265 |

\* cited by examiner

METHOD OF MAKING CATHETERS WITH ADDITIVES CONSOLIDATED INTO POLYMER WALL

RELATED APPLICATIONS

This application claims priority of U.S. Provisional Application No. 60/612,673 filed on Sep. 22, 2004, the content of which is incorporated herein by reference.

BACKGROUND OF THE INVENTION

1. Field of the Invention

The present invention relates generally to methods of manufacturing medical tubing. In particular, the present invention relates to methods of making catheters having additives consolidated into one or more base layers of nonextruded polymer material.

2. Description of the Related Art

Medical tubing and catheters are widely employed for a variety of treatment and diagnostic procedures involving, for example, the administration of fluid medications and devices into a patient and the removal of fluids from the patient. In this application, the terms "catheter" and "medical tubing" will be used interchangeably to refer to the same structure.

The ultimate use for which medical tubing is designed requires that the tubing have certain physical characteristics. For example, a catheter must be sufficiently stiff or rigid to enable its insertion and movement through narrow body orifices and channels and, in some applications, must also be able to withstand a high bursting pressure. On the other hand, a catheter must be sufficiently soft and flexible so that it may readily conform to body shapes so as not to cause injury to the interior wall of a patient's vessel as it is advanced. In addition, a catheter must be of sufficient mechanical strength to resist tearing during normal use, such as when the catheter is removed against tissue resistance.

In many medical devices, the polymer used to construct these devices is first compounded with additional agents, such as coloring agents, plastisizers, and opacifiers to obtain optimum properties of the medical device for which the polymer is used. Such compounding generally involves adding the desired additive to pellets of the polymer and running the mix through a compounder (e.g., an extruder) where the polymer is sheared apart and inherently blends with the polymer. After manufacturing, the devices are often coated with things to reduce friction, improve blood compatibility, or provide therapeutic benefits. Such surface coatings are difficult to accomplish because the surface must be prepared correctly and the coatings are often rubbed or worn off.

The Applicant previously developed a method for nonextrusion manufacturing of catheters, which is described in U.S. Pat. No. 6,030,371. In this existing method, a catheter is formed by spraying a fine polymer particulate, or solvenated polymer particulate, over a core to form a polymer shell of the catheter. The polymer material can be varied over the length of the catheter by using different hardness polymers to gradually vary the hardness of the catheter. The '371 patent suggests that the different hardness polymers can be colored to provide visual confirmation of the transition of hardness. The '371 patent also teaches the application of an opacifier material with the polymer material, or between layers of the polymer material. The polymer and opacifier materials are consolidated, for example, by heating in an oven.

Existing catheter manufacturing methods have not recognized the significant advantages that can be obtained by applying certain therapeutic agents, diagnostic agents, and/or other polymers for modifying the base polymer materials, as the catheter wall is being formed so that these agents or other polymers can be consolidated with the base polymer material.

SUMMARY OF THE INVENTION

The present invention provides a method of making catheters in which various additives are consolidated into the polymer walls of the catheters. The method includes providing a core having an outer surface, spraying a base polymer material over the outer surface of the core, spraying an additive material over or together with the base polymer material, and consolidating the additive material and the base polymer material together to form the catheter wall. The base polymer material and the additive material are each applied as a fine particulate powder or solution of fine particulate, which can be sprayed over an outer surface of the core and the catheter wall as the catheter is being formed. The additive material can be selected from several therapeutic agents, diagnostic agents, and/or polymers for modifying the base polymer materials. By applying the additive materials as the catheter wall is being formed, the additive material can be consolidated with the base polymer material either throughout the polymer wall or primarily on the outer surface of the polymer wall.

According to a broad aspect of the present invention, a method of making medical tubing is provided, comprising the steps of: providing a core having an outer surface; applying a nonextruded layer of base polymer material over a length of the outer surface of the core; applying a nonextruded layer of an additive material other than an opacifier over the base polymer material layer; and consolidating the additive material and the base polymer material together to form the medical tubing.

According to another broad aspect of the present invention, a method of making catheters is provided, comprising the steps of: spraying a base polymer material over an outer surface of a core; spraying an additive material other than an opacifier together with or over the base polymer material; and consolidating the additive material and the base polymer material together to form the catheter.

Numerous other objects and features of the present invention will be apparent to those skilled in this art from the following description wherein there is shown and described exemplary embodiments of the present invention, simply by way of illustration of the modes best suited to carry out the invention. As will be realized, the invention is capable of other different embodiments, and its several details are capable of modification in various obvious aspects without departing from the invention. Accordingly, the drawings and description should be regarded as illustrative in nature and not restrictive.

BRIEF DESCRIPTION OF THE DRAWINGS

The present invention will become more clearly appreciated as the disclosure of the present invention is made with reference to the accompanying drawings. In the drawings.

DETAILED DESCRIPTION OF THE INVENTION

A method of making a catheter with additives consolidated into the polymer wall according to the present invention will now be described in detail with reference to FIGS. 1 to 4 of the drawings.

Figure 1:
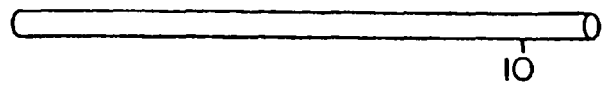
FIG. 1 shows a core mandrel over which a catheter will be constructed according to the present invention.

The method of making a catheter starts with a core mandrel 10, as shown in FIG. 1. The catheter will be constructed over the core mandrel 10 using much of the same technology disclosed in the Applicant's prior U.S. Pat. No. 6,030,371, which is incorporated herein by reference.

Figure 2:
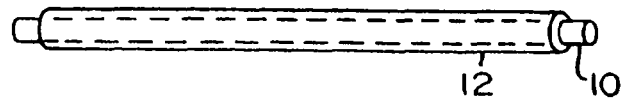
FIG. 2 shows a liner placed over the mandrel in the catheter manufacturing process of the present invention.

A catheter liner 12 is placed over the core mandrel 10, as shown in FIG. 2. The liner 12 can be formed of a variety of different materials but is generally less than 20% of the intended wall thickness. As an example, a liner having a 0.00150 inch wall thickness of TFE can be used. Alternatively, the process of the present invention can be performed without a liner, whereby a polymer material is applied directly on the mandrel 10.

Figure 3:
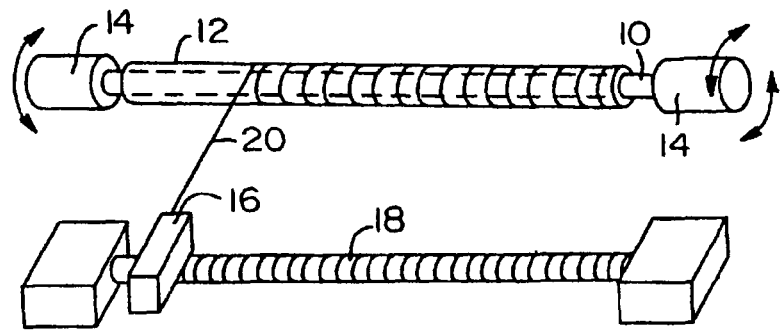
FIG. 3 shows a filament winding operation for applying a filament over the mandrel and liner in the catheter manufacturing process of the present invention.

A reinforcement filament is then applied over the liner 12, as shown in FIG. 3. During this operation, the mandrel/liner combination is loaded into rotating chucks 14. A filament winding head 16 travels on a screw carrier 18 longitudinally along the mandrel 10 to apply fibrous reinforcement filament 20 over the mandrel at a winding angle range of 0 to 90 degrees relative to the longitudinal axis of the catheter. For portions of the catheter that require great circumferential rigidity or kink resistance, a very tight winding angle (e.g., 80 to 90 degrees) of the reinforcement filament 20 can be used, and for portions of the catheter that require low rigidity, the reinforcement filament 20 can be applied in a low winding angle (e.g., 0 to 10 degrees). The winding angle of the reinforcement fiber 20 can be continuously varied over the length of the catheter by controlling the rotation speed of the mandrel 10 and the movement of the filament winding head 16 along the support 18.

Figure 4:
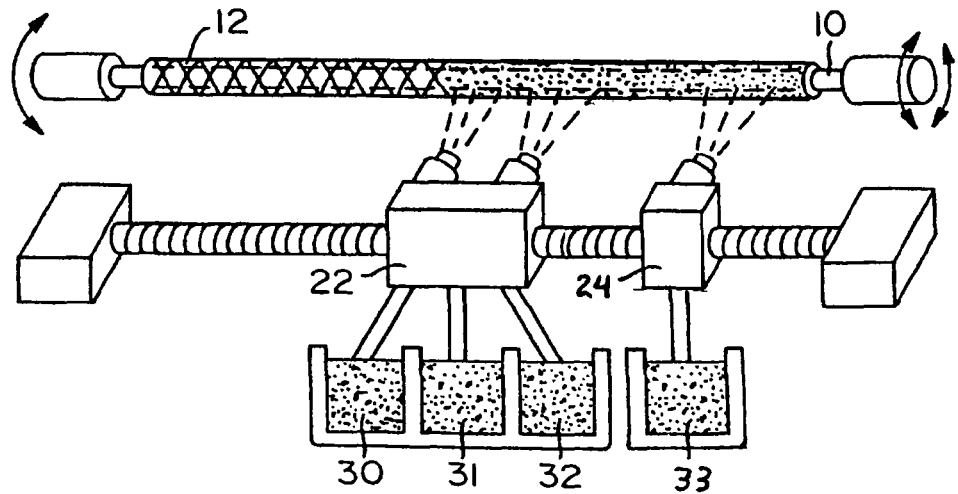
FIG. 4 shows a plurality of particulate materials being applied over the filament winding according to the catheter manufacturing process of the present invention.

At either the same time or after the reinforcement filament is applied, first and second atomizing spray heads 22 and 24 traverse the mandrel/liner, as shown in FIG. 4. The spray heads 22 and 24 apply atomized sprays that fuse to the substrate surface the sprays impinge upon (i.e., the mandrel 10, the liner 12, the reinforcement fiber 20, or the previous layer of polymer material). The substrate can be preheated to ensure complete fusion of the sprayed polymer to the substrate. This preheating can be accomplished with infrared, hot air, or resistance heating of the core mandrel 10 or other suitable means.

A suitable atomizing spray head 22 according to the present invention is described in detail in the Applicant's prior U.S. Pat. No. 6,030,371. The atomizing spray head 22 is connected to multiple containers 30 and 31 of polymer materials having varying degrees of hardness or other desired properties. In the preferred embodiment, the atomizing spray head 22 is also connected to a container 32 of an opacifier material, such as tungsten.

While the mandrel/liner is spinning, the atomizing spray head 22 traverses along a path parallel to the axis of the rotating mandrel/liner. As it traverses this path, a metering valve (not shown) can be set such that only the harder polymer (e.g., from the container 30) is applied at what will be the proximal end of the catheter. As the head 22 traverses the mandrel/liner, the metering valve is controlled such that it ports to the harder polymer to a lesser degree and to the softer polymer (e.g., from the container 31) to a higher degree until finally only the softest polymer is applied at the distal tip of the catheter, which will serve as the soft distal tip of the catheter. The different hardness polymer materials used in the present invention can be colored to provide visual confirmation of the transition of hardness.

In a similar fashion, opacifying powder can be selectively applied from the container 32. In one example, a single layer of polymer material can be applied as the filaments are placed. The single layer of polymer material can be followed by a layer of opacifier material and another layer of polymer material. A significant benefit of applying opacifier in this manner is that the movement of the head 22 can be paused momentarily to apply circumferential rings of high opacifier concentration, which serve as markers when the catheter is used under X-ray.

The present invention also includes the step of applying one or more additive materials to the catheter wall as the catheter is being formed. The additive materials are contained in one or more containers 33, as shown in FIG. 4, and are applied using the spray head 24. In one embodiment, the additive materials are applied by the spray head 24 during the application of the base polymer materials so that the additive materials are mixed with the base polymer materials during application and contained throughout the wall of the catheter. In another embodiment, the additive materials are applied as an over spray in which case the additive materials are adhered primarily to the outer surface of the catheter wall. The additive materials can be applied in fine particulate powder form or as fine particulate in a solution of solvent. By applying the additive materials in a particulate preform, the content and quantity of the additive materials can be varied continuously as the additive materials are being applied to provide variable properties over the length of the catheter. The additive materials are then consolidated together with the base polymer material to form the catheter. The consolidation is preferably accomplished by heating, but in some cases may be accomplished by other known techniques, such as driving off solvent from a solution.

The additive material can include polymer materials used to modify the base polymer material. For example, the additive material can be silicones, PTFE, paraffins, plastisizers and lubricants. The additive material can also include non-polymeric materials, such as therapeutic agents and diagnostic agents. For example, the additive material can be therapeutic agents such as anticoagulants, anti-inflamatories, oxides, and gene therapy materials. The additive material can also be diagnostic agents other than opacifiers, or coloring agents separate from the base polymer materials. For example, the diagnostic agent can be a metal.

After the base polymer material and the additive material are consolidated together, the catheter can be rough-sized by passing a cutter over the surface of the catheter and then polished. The catheter body is then removed from the rotating chucks 14 and is ready for finishing operations, such as curving or hubbing.

The method of the present invention can be performed by applying unmelted powders to a heated mandrel or liner. The mandrel 10 can be grounded and the powder material charged as the unmelted powders are applied, thereby causing the powders to electrostatically cling to the heated mandrel 10 or liner 12 during application. When the base polymer material impinges upon the heated mandrel 10 or liner 12, the powder melts to form a uniform coating over the surface thereof. A series of additional coating layers can be applied over the mandrel 10 or liner 12 by making several passes of the spray head 22 over the length or selected portions of the catheter. The additive material is then applied over the outer surface of the base polymer material using the spray head 24. The coated mandrel or liner can then be heated (e.g., baked in an oven) to consolidate the additive material with the base polymer material.

While the invention has been specifically described in connection with specific embodiments thereof, it is to be understood that this is by way of illustration and not of limitation, and the scope of the appended claims should be construed as broadly as the prior art will permit.

What is claimed is:

1. A method of making medical tubing, comprising the steps of:
    providing a core having an outer surface;
    applying a nonextruded layer of base polymer material over a length of said outer surface of the core;
    applying a nonextruded layer of an additive material other than an opacifier over said base polymer material layer; and
    consolidating said additive material and said base polymer material together to form the medical tubing;
    wherein said additive material is selected from the group consisting of silicones, PTFE, paraffins, plastisizers, lubricants, nonpolymeric therapeutic agents, nonpolymeric diagnostic agents, and coloring agents.

2. The method of making medical tubing according to claim 1, wherein said base polymer material and said additive material are each applied in powder form.

3. The method of making medical tubing according to claim 2, wherein said base polymer material and said additive material are consolidated together by heating.

4. The method of making medical tubing according to claim 1, wherein said base polymer material and said additive material are applied in a solution of solvent.

5. The method of making medical tubing according to claim 4, wherein said base polymer material and said additive material are consolidated together by driving off the solvent.

6. The method of making medical tubing according to claim 1, wherein said additive material comprises a second polymer material used to modify the base polymer material.

7. The method of making medical tubing according to claim 6, wherein said second polymer material is selected from the group consisting of silicones, PTFE, paraffins, plastisizers and lubricants.

8. The method of making medical tubing according to claim 1, wherein said additive material comprises a nonpolymeric material.

9. The method of making medical tubing according to claim 8, wherein said nonpolymeric material is a therapeutic agent.

10. The method of making medical tubing according to claim 8, wherein said therapeutic agent is selected from the group consisting of anticoagulants, anti-inflamatories, oxides, and gene therapy materials.

11. The method of making medical tubing according to claim 1, wherein said additive material is a diagnostic agent.

12. The method of making medical tubing according to claim 11, wherein said diagnostic agent is a metal.

13. The method of making medical tubing according to claim 1, wherein said additive material comprises a coloring agent.

14. A method of making catheters, comprising the steps of:
    spraying a base polymer material over an outer surface of a core;
    spraying an additive material other than an opacifier over said base polymer material; and
    consolidating said additive material and said base polymer material together to form the catheter;
    wherein said additive material is selected from the group consisting of silicones, PTFE, paraffins, plastisizers, lubricants, nonpolymeric therapeutic agents, nonpolymeric diagnostic agents, and nonpolymeric coloring agents.

15. The method of making catheters according to claim 14, wherein said base polymer material and said additive material are each sprayed in powder form.

16. The method of making catheters according to claim 15, wherein said base polymer material and said additive material are consolidated together by heating.

17. The method of making catheters according to claim 14, wherein said base polymer material and said additive material are each sprayed in solvenated form.

18. The method of making catheters according to claim 17, wherein said base polymer material and said additive material are consolidated together by driving off the solvent.

19. The method of making catheters according to claim 14, wherein said additive material is a polymeric material selected from the group consisting of silicones, PTFE, paraffins, plastisizers, and lubricants.

20. A method of making catheters, comprising the steps of:
    spraying a base polymer material over an outer surface of a core;
    spraying an additive material other than an opacifier together with or over said base polymer material; and
    consolidating said additive material and said base polymer material together to form the catheter;
    wherein said additive material is selected from the group consisting of silicones, PTFE, paraffins, plastisizers, lubricants, nonpolymeric therapeutic agents, nonpolymeric diagnostic agents, and coloring agents; and
    wherein said additive material is a therapeutic or diagnostic agent.

21. A method of making catheters, comprising the steps of:
    spraying a base polymer material over an outer surface of a core;
    spraying an additive material other than an opacifier together with or over said base polymer material; and
    consolidating said additive material and said base polymer material together to form the catheter;
    wherein said additive material is selected from the group consisting of silicones, PTFE, paraffins, plastisizers, lubricants, nonpolymeric therapeutic agents, nonpolymeric diagnostic agents, and coloring agents; and
    wherein said additive material is applied as an over spray to the base polymer material and adheres primarily to the outer surface of the catheter prior to consolidating the base polymer material and the additive material to form the catheter.

* * * * *